United States Patent
Labudde

(10) Patent No.: US 7,043,068 B2
(45) Date of Patent: May 9, 2006

(54) METHOD FOR DETECTING DISPLACEMENTS OF THE BRAIN AREAS AND THE REPRESENTATION THEREOF ON A DISPLAY, SAID DISPLACEMENTS CAUSED BY TUMOUR FORMATION

(75) Inventor: Dirk Labudde, Berlin (DE)

(73) Assignee: Forschungsverbund Berlin e.V., Berlin (DE)

( * ) Notice: Subject to any disclaimer, the term of this patent is extended or adjusted under 35 U.S.C. 154(b) by 696 days.

(21) Appl. No.: 10/221,064

(22) PCT Filed: Mar. 8, 2001

(86) PCT No.: PCT/DE01/00955

§ 371 (c)(1),
(2), (4) Date: Oct. 28, 2002

(87) PCT Pub. No.: WO01/67394

PCT Pub. Date: Sep. 13, 2001

(65) Prior Publication Data

US 2004/0013289 A1 Jan. 22, 2004

(30) Foreign Application Priority Data

Mar. 9, 2000 (DE) .............................. 100 13 360

(51) Int. Cl.
*G06K 9/00* (2006.01)
(52) U.S. Cl. ..................................... 382/132
(58) Field of Classification Search ..................... None
See application file for complete search history.

(56) References Cited

U.S. PATENT DOCUMENTS 5,633,951 A * 5/1997 Moshfeghi .................. 382/154
6,236,742 B1 * 5/2001 Handel ....................... 382/128

OTHER PUBLICATIONS

Kyriacou et al.: "Nonlinear Elastic Registration of Brain Images with Tumor Pathology Using a Biomechanical Model", IEEE Transactions on Medical Imaging, vol. 18, No. 7, Jul. 1999.

* cited by examiner

Primary Examiner—Jingge Wu
Assistant Examiner—Ashutosh Upreti
(74) Attorney, Agent, or Firm—Karl Hormann

(57) ABSTRACT

The invention relates to a method of detecting the displacement of individual brain areas and to the presentation thereof on a display for guaranteeing optimal planning of an operation, said displacements being caused by tumor formation. According to the invention a displacement vector is detected for each brain area which was situated at a defined location in the initial position where a tumor is located now. Said displacement vector defines the displacement of a brain area in the direction and the amount thereof, whereby said displacement is caused by tumor growth. Said vector is detected by means of two parameters (b and c) which can be derived from the size and the kind of the tumor. The displacement vectors are numerically calculated according to the formula $u_r = cr + br^{-2}$ after the two parameters have been detected. The image of the tumor as well as the detected displacements are subsequently inserted into a stereotactic atlas. The brain areas are displayed at the actual locations in the thus obtained image. Improved planning for carrying out operations can thus be guaranteed by means of said representation.

5 Claims, 1 Drawing Sheet

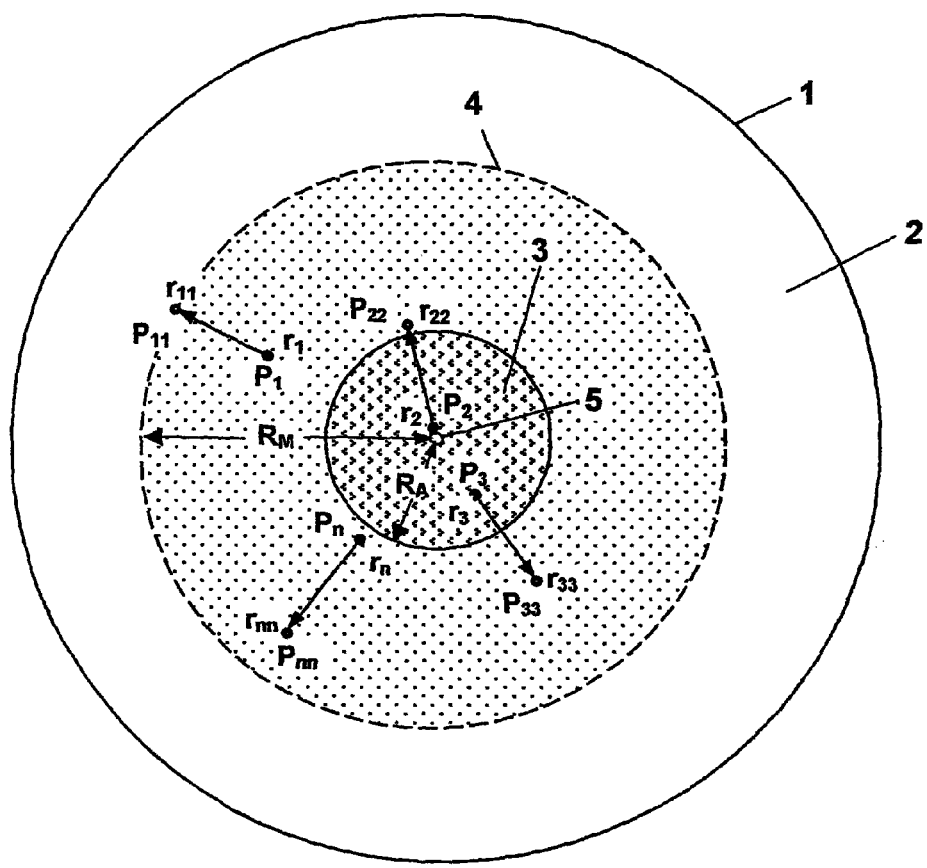

METHOD FOR DETECTING DISPLACEMENTS OF THE BRAIN AREAS AND THE REPRESENTATION THEREOF ON A DISPLAY, SAID DISPLACEMENTS CAUSED BY TUMOUR FORMATION

BACKGROUND OF THE INVENTION

1. Field of the Invention

The invention relates to a method of detecting brain area displacements as a result of tumor formation and their presentation on an image screen for purposes of ensuring optimum planning for an operation.

2. The Prior Art

In neurosurgery, the availability of efficient navigational devices by medical technology that conventionally guided stereotactic operating methods on a broad clinical basis were abandoned in favor of navigated interventions guided by image presenting controls. Neurosurgeons have at their disposal CD-versions of stereotactic atlases developed by Talairach and Schaltenbrand. Surgical access paths can now be monitored by atlas series which can be correlated with image series. It is thus possible to estimate risks even before an operation. The correlation also makes possible improved planning and provides important decision criteria for the execution of an operation, in the search for important anatomical land marks and physiological centers in the case of special procedures, e.g. Parkinson. The occurrence of brain tumors leads to spatial demands within the skull and, hence, to changes in pressure and local changes of brain areas.

The disadvantage of known atlases is that they do not take into consideration local changes, in particular local displacements of brain areas. Hence, they can be used on a limited scale only in surgery seeking to remove tumors.

OBJECTS OF THE INVENTION

It is an object of the invention to provide a method by which displacement of brain areas as a result of tumor formation may be detected and presented on an image screen by correlation with stereotactic atlases.

Other objects will in part be obvious and will in part appear hereinafter.

SUMMARY OF THE INVENTION

In accordance with the invention the object is accomplished by determining a displacement vector for each brain area which initially was located at a defined position and is now occupied by a tumor. The grown tumor will have displaced the cell tissue surrounding it. At the same time, this will have resulted in a deformation of the mass of the brain in the environment of the tumor. A mathematical model of this deformation can be established by means of vector functions. The position of each point of mass of an area within the brain may be described by a position vector in the predetermined coordinate system. As a result of the growth of the tumor the points of mass will change their position. This change in position may be described by a vector function. Every displaced point of mass will then be defined by a new position vector.

The displacement vector may be defined with sufficient accuracy by the equation $$\underline{u}(\underline{r}) = \underline{u}(0) + \underline{r}\phi(0)$$

wherein $\phi$ represents the distortion tensor. The distortion tensor is symmetrical and is defined by the expression $\phi = \text{grad } \underline{u}$.

As a result of tumor growth the structure of the tissue within a predetermined area of the environment of the tumor will lose its mechanical equilibrium. Within the cell tissue internal forces arise which are also defined as strains. The deformation occurs as a reaction to these strains. Thus, in addition to the distortion tensor $\phi$ the strain tensor $\psi$ is of decisive significance. In a state of equilibrium, outside of the previously mentioned area, the resultant of all internal strains disappears, so that $\psi = 0$. The correlation between the distortion tensor $\phi$ and the strain tensor $\psi$ is given by Hooke's law.

Forces effective at the immediate surface, such as the displacement by the tumor, are modeled by the following parameters. The displacement vector which in its direction and size defines the tumor induced displacement of a brain area is characterized by a first parameter $c_1$ and a second parameter $b_1$ both of which influence the effect of the displacement of points of mass. The two parameters $b_1$ and $c_1$ are a measure of the size of the tumor and of the effect of the tumor on its environment and may be deduced from these two boundary conditions. The size of the tumor may be derived directly from an image of the tumor provided by MRT or CT. The effect of a tumor on its environment which is defined by type, size and degree of the tumor may be determined from an image of the environment of the tumor. The area in which the tumor has an effect on its environment, i.e. where the tissue is not in a state of equilibrium, is defined by the maximum effect of the tumor. At a certain distance from the tumor corresponding to the maximum effect the position vectors will not have been subject to a change in position on account of the tumor formation. The maximum effect of the tumor may also be selected from empirically derived comparative values which may have been detected, for instance, on the basis of the type of tumor, the size of the tumor and other patient specific data. Subsequently, the individual displacement vectors for every effected point of mass will be numerically calculated on the basis of the equation $$u_r = cr + br^{-2}.$$

Once the individual displacement vectors have been calculated, the image of the tumor as well as the detected displacements which have occurred as a result of the tumor formation are inserted into a stereotactic atlas. In the presentation obtained in this manner, the brain areas will then be depicted in their actual positions.

Improved planning for the execution of surgery may be ensured by this presentation. It is also possible to use the presentation of the brain of a patient changed by the tumor formation for purposes of training for planning surgery. Furthermore, the data calculated and correlated with the stereotactic atlas may be used for controlling a surgical computer.

DESCRIPTION OF THE DRAWING

The novel features which are considered to be characteristic of the invention are set forth with particularity in the appended claims. The invention itself, however, in respect of its structure, construction and lay-out as well as manufacturing techniques, together with other objects and advantages thereof, will be best understood from the following description of preferred embodiments when read in connection with the appended drawings, in which:

FIG. 1 is a schematic presentation of displacement vectors for individual brain areas.

DESCRIPTION OF THE PREFERRED EMBODIMENT

The appended drawing is a schematic presentation of a skull 1 with a tumor 3 developed in a brain 2. Every one of the brain areas represented by the points of mass $P_1$, $P_2$, $P_3$, $P_n$ has been displaced from its initial location defined by the position vectors $r_1$, $r_2$, $r_3$, $r_n$, to a new position having the respective position vectors $r_{11}$, $r_{22}$, $r_{33}$, $r_{nn}$. This change in position is covered by the vector function $u$ ($r$). For a fixed point of mass $P_1$, $P_2$, $P_3$, $P_n$, $u$ ($r$) is also called displacement vector. The displaced mass point $P_{11}$ is then defined by the new position vector $r_{11}=r_1+u(r_1)$. The displacement vector for mass point P1 may be stated with sufficient accuracy as $$u(r_1)=u(0)+r_1\phi(0)$$

where $\phi$ connotes the distortion tensor. The distortion tensor is symmetrical and is defined by the expression $\phi=\mathrm{grad}\ u$. As a result of the tumor formation the surrounding tissue structure has lost its mechanical equilibrium. There are internal strains within the cell tissue which react by bringing about a deformation. Therefore, in addition to the distortion tensor $\phi$, the strain tensor $\psi$ is of decisive importance. In a state of equilibrium which exists at a finite distance from the center of the tumor 3 and which is defined by the maximum effect of the tumor, the resultant of all internal strains disappears, hence, div $\psi=0$. The correlation between distortion tensor and strain tensor is provided by Hooke's law. Accordingly, $$\Psi = \frac{E}{1+\sigma}\left(\Phi + \frac{3\sigma}{1-2\sigma}\Phi I\right)$$

where
E=elasticity module (Young's modulus);
$\sigma$=lateral contraction coefficient (Poisson's ratio);
I=the unity matrix; and $$\phi = \frac{1}{3}\sum_i \phi ii\ \text{the median distortion.}$$

By inserting this expression into the equation $$\mathrm{div}\ \psi=0$$

the result will be $$2(1-\sigma)\mathrm{grad\ div}\ u-(1-2\sigma)\mathrm{rot\ rot}\ u=0.$$

Forces acting on the immediate surface, such as the displacement by the tumor 3, are modeled by the following parameters.

At the margin of the tumor 3 the displacement vector may be read directly; it corresponds to the radius $R_A$ of the tumor 3. Proceeding from a single cell, i.e. the GO cell 5, the tumor 3 grew from size $r_o$ to its currently observed size $R_A$. At a sufficiently large distance $R_M$ from the tumor 3 the strain coincides with the brain pressure. This distance is defined as maximum effect 4. The phrase maximum effect is to be understood as a spatial range which is still affected by a displacement brought about by the tumor 3. Outside of this range, the presence of the tumor 3 causes no displacement of brain areas, and no shifting of points of mass occurs.

In the simplest case tissue displacement as a result of tumor growth takes place in a radial direction only. Proceeding from coordinates of a sphere, any shift in the $\phi$ and $\Theta$ direction disappears, and in the r direction it is only dependent from the distance r of any given point of mass $P_1$, $P_2$, $P_3$, $P_n$ from the center of the tumor 3. Hence, rot $u=0$, and grad div $u=0$ also. Therefore, div $u=$const, the constant being about 3 c. The definition of the divergence yields the equation $$u_r=cr+br^{-2}$$

for a shift in the r direction.

On the basis of this, the distortion tensor as well as the strain tensor may be calculated. Thus, radial strain may be defined as $$\Psi_\pi = \frac{E}{1-2\sigma}c - \frac{2E}{1+\sigma}br^{-3}$$

Taking into account the previously mentioned boundary conditions, the parameters b and c may be calculated on the basis of two equations.

The following values are assumed for the selected example:
$R_A$=20 mm size of tumor 3;
$R_M$=50 mm maximum effect 4;
$r_o$=30 □m size of starting cell 5;
E=7.16.10$^1$ Pa elasticity module;
$\sigma$=0.33 lateral contraction coefficient;
$p_{Hirn}$=1.172 kPa brain pressure It is possible mathematically to calculate the parameters b and c on the basis of the published value $r_o$, a starter cell or GO cell 5, as well as of the material constants E, $\sigma$, $p_{Hirn}$ and of the determined instantaneous value $R_A$ and the maximum effect $R_M$ of the tumor 3. It is done by the following equations:

$$\Psi_\pi = \frac{E}{1-2\sigma}c - \frac{2E}{1+\sigma}bR_M^{-3} = P_{Hirn} \quad [1]$$

and $$u_{RA}=cr_o+br_o^{-2}. \quad [2]$$

The constant b may be defined by means of the equation for the radial strain $\psi_n$. However, for the present purpose the radial strain must be set to equal the brain pressure, and the size $R_M$ (radius of the maximum effect 4) has to be defined for this equilibrium. It is to be assumed that $R_M$ depends upon the type of tumor since the effect of the tumor 3, i.e. the induced displacements depend significantly on the type of tumor (e.g. its consistency). In other words, each type of tumor will have to be described in terms of a characteristic maximum effect 4. The term maximum effect 4 is intended to mean a spatial area in which the tumor 3 still causes a displacement. The maximum effect 4 may also be determined by a visual evaluation of examinations (e.g. by MRT, CT). Outside of the boundaries of this areas the presence of the tumor does not lead to any displacement of brain areas. The maximum effect 4 may also be determined by automatic image recognition or image evaluation methods. However, empirically determined values depending upon the type of the tumor and the size of the tumor (degree) which may be used to define parameter b, are also available. To this end recourse may be had to a data base which takes into account the correlation between maximum effect and size of tumor, degree of tumor, as well as the specific condition of the patient such as, for instance, his sex, age, location of the tumor, and a current health profile or treatment.

On the basis of equation [2] the value of parameter c is as follows:

$$c = \frac{2}{3}10^3 - 3.70410^{13} \text{ mm}^3 b. \quad [3]$$

Proceeding from equation [1], parameter b may be determined by the following steps, by first entering the value for parameter c from equation [3]:

$$p_{Him} = \frac{E}{1-2\sigma}\left(\frac{2}{3}10^3 - 3.70410^{13} \text{ mm}^3 b\right) - \frac{2E}{1+\sigma}bR_M^{-3}.$$

A further transposition of this equation initially results in $$p_{Him} = \frac{E}{1-2\sigma}\frac{2}{3}10^3 - \frac{E}{1-2\sigma}3.70410^{13} \text{ mm}^3 b - \frac{2E}{1+\sigma}bR_M^{-3}$$

followed by $$p_{Him} = \frac{E}{1-2\sigma}\frac{2}{3}10^3 - b\left(\frac{E}{1-2\sigma}3.70410^{13} \text{ mm}^3 + \frac{2E}{1+\sigma}bR_M^{-3}\right).$$

Therefore, the resulting equation for solving parameter b is:

$$b = -\frac{p_{Him} - \frac{E}{1-2\sigma}\frac{2}{3}10^3}{\left(\frac{E}{1-2\sigma}3.70410^{13} \text{ mm}^3 + \frac{2E}{1+\sigma}R_M^{-3}\right)} \quad [4]$$

Parameter b having thus been calculated on the basis of the initial values, its value may be inserted into equation [3] to calculate parameter c. Once parameters c and b have been determined, each displacement $u_r$ for each individual point of mass $P_1$, $P_2$, $P_3$, $P_n$ which in its initial state, i.e. before tumor 3 developed, was located at a position within $R_M$, may be unambiguously calculated.

The displacement vectors $\underline{u}(\underline{r})$ for each point of mass $P_1$, $P_2$, $P_3$, $P_n$ thus calculated are determined by suitable software in order to obtain the new position vectors $r_{11}$, $r_{22}$, $r_{33}$, $R_{nn}$. The new coordinates for the displaced points of mass $P_{11}$, $P_{22}$, $P_{33}$, $P_{nn}$ are inserted into existing stereotactic or digitized anatomic atlases to make visualization possible of the changes of brain areas resulting from the tumor formation.

It is thus possible during the planning stages of surgery to take displacements of areas into account. It is then that meaningful use may be made of the correlation of anatomic atlases and image series (CT/MRT) of an infected patient.

What is claimed is:

1. A method of determining displacements of brain areas as a result of tumor formation and of their presentation on an image screen utilizing stereotactic atlases characterized by determining by means of known physical correlations, particularly Hooke's law, a displacement vector $\underline{u}(\underline{r})$ for each point of mass of a brain area ($P_1$, $P_2$, $P_3$, $P_n$) which in an initial state was located at a position described by a position vector ($r_1$, $r_2$, $r_3$, $r_n$) where the tumor (3) is now located, which displacement vector may be unambiguously defined by two parameters b, c, whereby the parameters b, c may be derived from the boundary conditions tumor size and tumor type and the displacement vectors $\underline{u}(\underline{r})$ are subsequently mathematically calculated and a new position vector ($\underline{r}_{11}$, $\underline{r}_{22}$, $\underline{r}_{33}$, $\underline{r}_{nn}$) is calculated for each point of mass of a brain area ($P_1$, $P_2$, $P_3$, $P_n$) as a result of the displacement, thereafter inserting the image of the tumor (3) as well as the determined displacements with the new position vectors ($\underline{r}_{11}$, $\underline{r}_{22}$, $\underline{r}_{33}$, $\underline{r}_{nn}$) which took place as a result of the tumor formation, into an anatomic atlas so that the brain areas characterized by the displaced points of mass ($P_{11}$, $P_{22}$, $P_{33}$, $P_{nn}$) are now displayed in the actual positions.

2. The method of claim 1, characterized by the fact that the parameters b, c are determined from an image of the tumor (3), in particular the size of the tumor and from an additional evaluation of the effects of the tumor formation by determining the maximum effect on the environment of the tumor (3).

3. The method of claim 1, characterized by the fact that the effect of the tumor formation on the environment of the tumor (3) which is characterized by the maximum effect, is determined from empirically determined correlations depending upon the type of tumor, the size of the tumor and further patient specific data.

4. The method of claim 3, characterized by the fact that the parameters b, c are determined by image recognition methods.

5. The method of claim 1, characterized by the fact that the displacement vectors $\underline{u}(\underline{r})$ for each point of mass of a brain area ($P_1$, $P_2$, $P_3$, $P_n$) are determined by the equation $U_r = cr + br^{-2}$.

* * * * *